United States Patent
Joyeux et al.

(10) Patent No.: US 10,893,854 B2
(45) Date of Patent: Jan. 19, 2021

(54) BIOMEDICAL DEVICE FOR WATERTIGHT SEALING OF AN OPENING

(71) Applicants: Luc Joyeux, Herent (BE);
Jean-Jacques Bondonneau, Mere (FR);
KATHOLIEKE UNIVERSITEIT LEUVEN, Leuven (BE)

(72) Inventors: Luc Joyeux, Herent (BE);
Jean-Jacques Bondonneau, Mere (FR)

(73) Assignees: Luc Joyeux, Herent (BE);
Jean-Jacques Bondonneau, Mere (FR);
KATHOLIEKE UNIVERSITEIT LEUVEN, Leuven (BE)

( * ) Notice: Subject to any disclaimer, the term of this patent is extended or adjusted under 35 U.S.C. 154(b) by 292 days.

(21) Appl. No.: 15/531,307

(22) PCT Filed: Nov. 27, 2015

(86) PCT No.: PCT/EP2015/077974
§ 371 (c)(1),
(2) Date: May 26, 2017

(87) PCT Pub. No.: WO2016/083606
PCT Pub. Date: Jun. 2, 2016

(65) Prior Publication Data
US 2017/0340315 A1    Nov. 30, 2017

(30) Foreign Application Priority Data
Nov. 28, 2014 (EP) .................... 14195542

(51) Int. Cl.
*A61B 17/00* (2006.01)
*A61B 17/42* (2006.01)

(52) U.S. Cl.
CPC .............. *A61B 17/0057* (2013.01); *A61B 2017/00004* (2013.01); *A61B 2017/00575* (2013.01);
(Continued)

(58) Field of Classification Search
CPC ......... A61B 17/0057; A61B 17/12022–12195; A61B 17/11–1146;
(Continued)

(56) References Cited

U.S. PATENT DOCUMENTS 4,878,890 A * 11/1989 Bilweis ..................... A61F 2/00
600/37
8,016,857 B2 * 9/2011 Sater .................. A61B 17/0057
606/213
(Continued)

FOREIGN PATENT DOCUMENTS

EP       1836968 A1    9/2007
WO    2004/024030 A1    3/2004
(Continued)

OTHER PUBLICATIONS

R. Papanna et al., "Absorbable gelatin plug does not prevent iatrogenic preterm premature rupture of membranes after fetoscopic laser surgery for twin—twin transfusion syndrome", Ultrasound Obstet Gynecol, 2013, pp. 456-460, vol. 42, Issue 4.
(Continued)

*Primary Examiner* — Richard G Louis
(74) *Attorney, Agent, or Firm* — Nixon & Vanderhye

(57) ABSTRACT

Disclosed is a biomedical device being introduced by a hollow tube having a longitudinal axis in a subject in a minimally invasive surgery procedure for watertight sealing of an opening including at least two assemblies, each assembly including one flap connected to one arm, the arm having an longitudinal axis; the assemblies including a delivery configuration, a deployed configuration, and a sealed configuration and outwards deployment unit for switching from the delivery configuration to the deployed configuration and inwards deployment unit for switching from the deployed configuration to the sealed configuration.
(Continued)

Also disclosed is a kit of parts including an outer hollow tube, an inner hollow tube, and a related biomedical device.

26 Claims, 9 Drawing Sheets

(52) U.S. Cl.
CPC ............ *A61B 2017/00588* (2013.01); *A61B 2017/00597* (2013.01); *A61B 2017/00606* (2013.01); *A61B 2017/00619* (2013.01); *A61B 2017/00623* (2013.01); *A61B 2017/00637* (2013.01); *A61B 2017/00862* (2013.01); *A61B 2017/00867* (2013.01); *A61B 2017/4216* (2013.01)

(58) Field of Classification Search
CPC .............. A61B 2017/00575–00632; A61B 2017/00637–00641; A61B 2017/00672–00676; A61B 17/12004; A61B 17/1205–12127; A61B 17/1103–1142; A61F 2/0063; A61F 2002/0068–0072
See application file for complete search history.

(56) References Cited

U.S. PATENT DOCUMENTS

| | | |
|---|---|---|
| 8,791,219 B2 | 7/2014 | Grubbs et al. |
| 9,445,797 B2 * | 9/2016 | Rothstein ............ A61B 17/0057 |
| 9,687,242 B2 * | 6/2017 | Hendriksen ...... A61B 17/12022 |
| 2006/0241687 A1 * | 10/2006 | Glaser ................ A61B 17/0057 606/213 |
| 2006/0259074 A1 * | 11/2006 | Kelleher ................ A61B 17/04 606/213 |
| 2007/0225756 A1 | 9/2007 | Preinitz et al. |
| 2008/0077180 A1 * | 3/2008 | Kladakis ............ A61B 17/0057 606/216 |
| 2010/0106171 A1 * | 4/2010 | Arepally ................ A61B 17/11 606/153 |
| 2010/0268316 A1 * | 10/2010 | Brenneman .......... A61B 17/083 623/1.11 |

FOREIGN PATENT DOCUMENTS

| | | |
|---|---|---|
| WO | 2012/170493 A1 | 12/2012 |
| WO | 2013/072517 A1 | 5/2013 |

OTHER PUBLICATIONS

International Search Report, dated Mar. 10, 2016, from corresponding PCT application.

\* cited by examiner

BIOMEDICAL DEVICE FOR WATERTIGHT SEALING OF AN OPENING

FIELD OF INVENTION

The present invention relates to a biomedical device. In particular the present invention relates to a biomedical device for watertight sealing of an opening after a minimally invasive surgery.

BACKGROUND OF INVENTION

Minimally Invasive Surgery (MIS) is a surgical procedure less invasive than open surgery used for similar indications. It decreases patient's morbidity and allows patients to have less pain and to return to their daily activities more quickly. MIS includes many surgical procedures: endoscopic techniques, laparoscopy (digestive, urologic and gynecological surgery), thoracoscopy, mediastinoscopy, cervicoscopy, robotic surgery and fetoscopy (maternal-fetal surgery). MIS is carried out through the wall of a body cavity or through an anatomical opening. MIS typically involves use of endoscope and long instruments inserted inside the body through trocars. These instruments are manipulated by the surgeon to perform an operation with indirect observation of the surgical field through an endoscope displayed on a large-scale video screen.

More particularly, among MIS techniques, fetoscopy is a delicate maternal-fetal procedure performed during pregnancy that allows access to the living fetus, the amniotic cavity, the umbilical cord, and the placenta by means of a small endoscope (fetoscope) inserted through the abdominal wall and uterus into the amniotic cavity. Fetoscopy is indicated for diagnostic and therapeutic means, such as sampling of amniotic fluid or cord blood, laser coagulation of abnormal placental blood vessels in some *twin* pregnancies, tracheal occlusion in severe congenital diaphragmatic hernia, or surgical repair of open spina bifida. However, such invasive fetoscopic techniques are frequently complicated by amniotic fluid leakage, separation of amnion and chorion or iatrogenic preterm premature rupture of membranes (iPPROM) which may cause premature preterm labor and birth, leading to the fetal death in the worst cases. It is to note that the human amnion is a thin non-vascularized membrane preventing suitable and efficient healing process. Therefore, successful sealing of the defect site has the potential to prolong the pregnancy, thereby reducing perinatal morbidity.

For all MIS procedure, after placement of a trocar, the trocar opening needs to be closed to avoid post-operative complications, particularly trocar site hernia, loss of body fluids or infections. The closure remains difficult due to tissue wall thickness preventing efficient internal closure.

Various techniques have been proposed to close trocar opening following an MIS procedure.

For classical MIS laparoscopic techniques, closure is usually done with placement of sutures under direct endoscopic vision with the use of a device guiding a needle during suturing of an incision. For instance WO 2013/072517 discloses a surgical device for coupling with a trocar and comprising one needle guide channel. While there are numerous products available for suturing the trocar incision, suturing implies a series of traumatic manipulations to complete a single suturing such as pushing, pulling, retraction of the wound, and insertion/extraction of a needle. Furthermore, considerable stress or tension is applied upon suture system since it prevents organs or tissues from protruding through the aperture formed by trocar opening. Pulling threads or stitches may cause trauma to the adjacent tissue of the body wall. In fact due to unevenly distributed tension applied upon stiches, skin-underlying tissue may be torn or damaged weakening the suture and subcutaneous nerve may be compressed causing secondary pain for the patient. Moreover, traumatized tissue can impede new tissue growth over the suturing system which may lead to enlarge the weak area and to subsequent surgery for performing additional repairs. Therefore, suturing the trocar opening is opposed to the "minimal damage" basis of MIS.

In the case of fetoscopic procedure, closure may be done with the use of biomedical adhesives. For instance U.S. Pat. No. 8,791,219 discloses a copolymer, comprising separate water-soluble units, interfacial adhesive units and cross linkable units, used as a sealant for preventing amniotic fluid from leaking. The injectable sealant is brought near to the uterus and the fetal membrane and injected into the interface between the uterus muscle and the fetal membrane. When a trocar, introduced through the uterus muscle, sealant and membrane, is removed, the sealant should prevent the amniotic fluid from leaking. Another approach disclosed by R. Papanna in "*Absorbable gelatin plug does not prevent iatrogenic preterm premature rupture of membranes after fetoscopic laser surgery for twin-twin transfusion syndrome*" (Ultrasound Obstet Gynecol. 2013; 42(4):456-60) is to provide a Chorioamniotic plug (CAP) made of a bioabsorbable gelatin sponge. The CAP is placed under ultrasound guidance to seal the trocar entry site in the chorioamniotic layers to promote healing. However, results show that CAP placement did not reduce iPPROM rates. Moreover, gelatin plugs tended to swell when soaked in amniotic fluid and this distension may lead to stretch the membrane defect. The gelatin also tends to lose its effectiveness once it becomes a dissolvable gel as time elapses.

A third approach in classical MIS laparoscopic techniques consist in closing the tissue opening by pressing a sheet against the tissue wall. For example WO 2004/024030 discloses an intra-abdominal mesh plate, lying against the inner wall of the body wall opening, connected to a double ear-piece designed for being anchored to the outer structure of the aperture, thus blocking the device into the desired position. The double ear-piece is intended to be manually pushed inside the body in order to put it into its gaps which is a not suitable in case of delicate procedure such as fetoscopy. Moreover, said double ear-piece does not guarantee a watertight closure. European patent application EP 1 836 968 discloses a closure device comprising a first set of struts and a second set of struts, each set of struts being provided with a hinge so that the first and the second sets of struts may be moved radially away from a longitudinal axis. Each strut may be covered with a thin membrane, so that in the deployed configuration, the closure device sandwiches an atrial septum and closes a septal defect. International application WO 2012/170493 relates to a device including a biodegradable patch formed of a flexible body which may be foldable into a delivery instrument. The patch is formed with a single sheet wherein a plurality of sharp protrusions is formed along a peripheral edge of a face of the body. The foldable patch may be delivered and deployed by means of a hollow trocar to the target opening. The positioned and deployed patch is anchored by embedding protrusions within the inner surrounding aperture tissue. Nevertheless, this system only covers the opening but does not watertightly close it. Moreover protrusions in the form of teeth or barbs that extend outwardly in contact with the surrounding tissue of the aperture provide an anchoring but also cause local tissue irritation and pain for the patient. It even causes the formation of micro-incisions in the tissue leading to fluid leakage, particularly in case of movement and/or high pressure against the wall tissue.

Therefore, there is still a need for an alternative biomedical device for watertight closing an of opening after MIS, which could be used during any MIS procedures such as delicate fetoscopy, which avoid trauma to the surrounding tissue (unlike sutures), which does not swell (unlike biomedical adhesive) and which does not require direct vision to the surgical site (unlike sutures, biomedical adhesives and sheets).

SUMMARY

The present invention meets those needs by providing a biomedical device which is inserted into a body cavity before the beginning of a MIS and which can seal in a watertight manner the trocar opening once the MIS has been performed; said trocar being inserted, during the MIS, into the body cavity through the biomedical device.

So, the biomedical device of the present invention is inserted into a body cavity before the beginning of any MIS, ensures the access of an inner hollow tube (e.g. a trocar) to the body cavity and then seals in a watertight manner the hollow tube opening without the use of suture or biological adhesives. Moreover, the biomedical device does not require direct vision to the surgical site in order to ensure the watertight sealing of the opening as it is already in the body cavity from the beginning of the MIS.

Thus the present invention relates to a biomedical device being introduced by an outer hollow tube having a longitudinal axis in a subject during a MIS procedure for watertight sealing of an opening, such as a trocar opening, the said biomedical device comprising:

at least two assemblies, each assembly comprising a proximal end and a distal end and one flap connected to one arm, said arm having an longitudinal axis; and assembling means connected to the at least two assemblies, said assembling means being configured such that the proximal end of each assembly is located on the same plane transverse to the longitudinal axis of the outer hollow tube;

the assemblies comprising a delivery configuration, a deployed configuration, and a sealed configuration and outwards deployment means for switching from the delivery configuration to the deployed configuration and inwards deployment means for switching from the deployed configuration to the sealed configuration; wherein in the delivery configuration, the flap and the arm of each assembly are aligned in the longitudinal axis of the arm, each assembly extends along a direction substantially parallel to the longitudinal axis of the outer hollow tube and the at least two assemblies together form a hollow cylinder for receiving an inner hollow tube therethrough; the axis of the hollow cylinder being the longitudinal axis of the outer hollow tube; in the deployed configuration, the flap of each assembly remains in the delivery configuration and the arm of each assembly is deployed outwardly relative to the longitudinal axis of the outer hollow tube and positioned at substantially 90° relative to its position in the delivery configuration; and in the sealed configuration, the flap of each assembly is deployed inwardly relative to the longitudinal axis of the outer hollow tube and positioned at substantially 90° relative to its position in the delivery configuration, and the arm of each assembly remains in the deployed configuration.

According to one embodiment, the biomedical device further comprises a membrane, connecting the arms and optionally the flaps of each assembly, which is stretched out upon deployment of the arm from the delivery configuration to the deployed configuration. According to one embodiment, the biomedical device comprises at least one assembling means connecting the arms and optionally the flaps of each assembly. According to one embodiment, the assembling means is selected among at least one membrane and/or at least one elastic band and/or at least one thread and/or at least one ribbon.

According to one embodiment, at least one flap comprises a first passage extending through the flap from an opening in the outer surface of the flap to an opening in the inner surface of the flap. According to one embodiment, at least one arm comprises a first passage extending through the arm from an opening in the proximal outer surface of the arm to an opening in the distal outer surface of the arm.

According to one embodiment, the outwards deployment means comprises at least one thread fixed at the opening in the proximal outer surface of at least one arm, passing through the first passage of the arm from the opening in the proximal outer surface of the arm to the opening in the distal outer surface of the arm, passing through the first passage of the flap of the corresponding assembly from the opening in the outer surface of the flap to the opening in the inner surface of the flap and extending out.

According to one embodiment, the flap of each assembly comprises a connecting passage extending across a part of the flap, preferably across the distal part of the flap. According to one embodiment, at least one flap comprises a second passage extending through the flap from the connecting passage to an opening in the inner surface of the flap. According to one embodiment, the inwards deployment means comprises a thread connecting the flap of each assembly together through the connecting passage of each flap, passing through the second passage of one flap from the connecting passage to the opening in the inner surface of said flap and extending out.

According to one embodiment, the flap of each assembly comprises a connecting portion and the arm of each assembly comprises a connecting portion connected to the connecting portion of the flap.

According to one embodiment, the biomedical device comprises 2, 3, 4, 5, 6, 7, 8, 9, 10, 11 or 12 assemblies.

According to one embodiment, each assembly is made from a bioabsorbable material, preferably polydioxanone (PDS). According to one embodiment, the membrane is made from a bioabsorbable material, preferably polyglactine 910. According to one embodiment, the outwards and/or the inwards deployment means (3, 4) is made from a bioabsorbable material, preferably polydioxanone (PDS). According to one embodiment, the outwards and/or the inwards deployment means (3, 4) is made from a bioabsorbable material, preferably polyglactine 910.

According to one embodiment, the biomedical device further comprises a means for maintaining the inwards deployment means deployed, preferably at least a clip or at least a surgical forceps or at least a V-shaped notch configured for keeping at least one thread under tension. According to one embodiment, the biomedical device further comprises a means for maintaining the outwards deployment means deployed, preferably at least a clip or at least a surgical forceps or at least a V-shaped notch configured for keeping at least one thread under tension.

According to one embodiment, the biomedical device further comprises an anchoring ring having an outer diameter substantially equal to the length of one assembly in the delivery or sealed configuration along the longitudinal axis; said anchoring ring comprising the means for maintaining the outwards and inwards deployment means deployed.

The present invention also relates to a kit of parts comprising:
- an outer hollow tube;
- an inner hollow tube; wherein said inner hollow tube has a smaller diameter than the outer hollow tube;
- a biomedical device according to the present invention; and
- optionally, an anchoring ring;

wherein said biomedical device is configured:
- for being positioned between said inner and outer hollow tubes in a delivery configuration; the inner hollow tube, the outer hollow tube and the biomedical device having the same longitudinal axis in said delivery configuration; and
- for being axially moveable along said longitudinal axis, especially relative to the outer hollow tube and the inner hollow tube.

Definitions

In the present invention, the following terms have the following meanings:
- "Arm" refers to an elongated part (i.e. having a dimension larger than the two others). In the present invention, the arm comprises a pressing portion and a connecting portion, said connecting portion being connected to a flap and is mobile about the axis of the connection.
- "Bioabsorbable" means that the material is resorbable by means of biological process, preferably in less than a few weeks or months depending on the material. Synonyms of bioabsorbable include bioresorbable and biodegradable.
- "Close" associated with the terms arm or flap refers to the relative position of said arm or flap with respect to the longitudinal axis of the hollow tube used for introducing the biomedical device in the delivery configuration, said position defining the configuration of the occluding biomedical device (i.e. the delivery, the deployed and the sealed configurations). A flap is closed when the flap is oriented in a substantially perpendicular direction relative to the longitudinal axis (in the sealed configuration). An arm is closed when the arm is oriented in a substantially parallel direction relative to the longitudinal axis (in the delivery configuration).
- "Distal part" refers to a part of the biomedical device which is located away from an operator (e.g. a surgeon) or a point of reference (e.g. the position of the surgical incision allowing penetration through the body of a subject) when the device is in the delivery configuration. The term distal always refers to the relative position of a part of the device in the delivery configuration.
- "Flap" refers to a shutter or a clapper. In the present invention, the flap comprises an occluding portion and a connecting portion, said connecting portion being connected to an arm and is mobile about the axis of the connection.
- "Hollow tube" refers to a hollow cylindrical rod. In the sense of the present invention hollow tube includes the term "trocar".
- "Inner" refers to the surface of the flap and the arm forming the internal surface of the cylinder formed or designed by the at least two assemblies together in the delivery configuration.
- "Invasive procedure" or "open surgery" refers to an open-air surgical procedure that requires a unique large and deep opening to access any body cavity.
- "Minimally invasive surgery" (MIS) is an endoscopic surgical procedure performed through the body wall (e.g. the skin) into a body cavity without large skin opening (e.g. less than 20 mm large, preferably less than 12 mm large). The endoscope and the instruments are inserted into the cavity through a skin opening inside metallic tubes (trocars). The endoscope connected to a dedicated video camera films the surgical field and diplays the endoscopic images in real-time on a monitor (video screen). The surgeon realizes the surgery with these instruments watching the surgical field on the monitor. MIS includes mainly the following techniques: endoscopic procedures, laparoscopy (digestive, urologic and gynecological surgery), thoracoscopy, mediastinoscopy, cervicoscopy, robotic surgery, embryoscopy and fetoscopy (maternal-fetal surgery).
- "Outer" refers to the surface of the flap and the arm forming the external surface of the cylinder formed or designed by the at least two assemblies together in the delivery configuration.
- "Open" associated with the terms arm or flap refers to the relative position of said arm or flap with respect to the longitudinal axis of the occluding biomedical device, said position defining the configuration of the occluding biomedical device (i.e. the delivery, the deployed and the sealed configurations). A flap is open when a flap is oriented in a substantially parallel direction relative to the longitudinal axis (in the delivery and deployed configurations). An arm is opened when the arm is oriented in a substantially perpendicular direction relative to the longitudinal axis (in the deployed and sealed configurations).
- "Opening" corresponds to a body wall opening which is not a natural orifice. For example, the opening is created by a surgical incision of a body wall followed by the insertion of a hollow tube through the incision to enter a body cavity (e.g. a trocar).
- "Proximal part" refers a part of the device which is located near an operator (e.g. a surgeon) or a point of reference (e.g. the position of the surgical incision allowing penetration through the body of a subject) when the device is in the delivery configuration. The term proximal always refers to the relative position of the part in the delivery configuration.
- "Subject" refers to an animal, preferably a mammal, more preferably a human. In one embodiment, a subject may be a "patient", i.e. a warm-blooded animal, more preferably a human, who/which is was/is/will be the object of a medical procedure, or is monitored for the development of a disease.
- "Substantially" refers, when used in conjunction with a numerical value, to the variation above or below 5% of said value.

"Suture" refers to stitches, row of stitches, staples, threads, coils, clips, glue, fasteners or any surgical attachment known by one skilled in the art creating an incision or a micro-opening into the tissue of a patient.

"Trocar" is a medical device that is made up, from the outside to the inside, of 3 parts: an obturator (sharpened tip), a cannula (hollow tube) and a seal. It is inserted through a body wall opening inside a body cavity. This tool functions as a portal for the placement of MIS instruments that slide in and out to reach the surgical field, and minimizes damage on the skin and body wall during the intervention. Within the present invention, it is referred to as an inner hollow tube.

"Watertight sealing" means that the body wall opening is sealed such that no fluid (e.g. a gas or a liquid) may enter or pass through the body wall opening. Such watertight sealing is achieved in the present invention by closing the body wall opening with the sealed configuration of biomedical device (i.e. with the flaps closed and the arms opened).

Within the present description the terms "outwards" and "inwards" are relative to the same reference, preferably relative to the longitudinal axis (A).

DETAILED DESCRIPTION

In one aspect, this invention relates to a biomedical device being introduced by a hollow tube having a longitudinal axis (A) in a subject during a MIS procedure for watertight sealing of an opening, said biomedical device comprising:
at least two assemblies, each assembly comprising one flap (1) connected to one arm (2), said arm (2) having a longitudinal axis (B);
the assemblies comprising a delivery configuration, a deployed configuration, and a sealed configuration and outwards deployment means (3) for switching from the delivery configuration to the deployed configuration and inwards deployment means (4) for switching from the deployed configuration to the sealed configuration; wherein
in the delivery configuration, the flap (1) and the arm (2) of each assembly are aligned in the longitudinal axis (B) and the at least two assemblies together form or design a cylinder having the longitudinal axis (A);
in the deployed configuration, the flap (1) of each assembly remains in the delivery configuration and the arm (2) of each assembly is deployed outwardly and positioned at substantially 90° relative to its position in the delivery configuration; and in the sealed configuration, the flap (1) of each assembly is deployed inwardly and positioned at substantially 90° relative to its position in the delivery configuration, and the arm (2) of each assembly remains in the deployed configuration.

Each assembly comprises a proximal end and a distal end. According to one embodiment, the biomedical device comprises assembling means connected to the at least two assemblies, said assembling means being configured such that the proximal end of each assembly is located on a same plane transverse (or perpendicular) to the longitudinal axis (A). In an alternative embodiment, the biomedical device comprises assembling means connected to the at least two assemblies, said assembling means being configured such that the connection between the respective flap and arm of each assembly is located on a same plane transverse (or perpendicular) to the longitudinal axis (A).

According to one embodiment, the biomedical device is configured for surrounding an inner hollow tube and for being introduced by an outer hollow tube.

According to one embodiment, in the sealed configuration the flap (1) of each assembly is deployed inwardly and positioned at substantially 90° relative to its position in the delivery configuration so that the edges of the flap are in contact with another flap.

According to one embodiment, in the delivery configuration, each assembly extends along a direction substantially parallel to the longitudinal axis (A). According to one embodiment, in the delivery configuration, the assemblies of the biomedical device form or design a cylinder enabling access of an inner hollow tube to a body cavity, said body cavity being delimited by a biological tissue, a body wall or a biological membrane. Especially, in one embodiment, the at least two assemblies together form a hollow cylinder for receiving an inner hollow tube (e.g. a trocar) therethrough, the axis of the said hollow cylinder being the longitudinal axis (A). Said access enables performing any MIS procedure therethrough. According to one exemplary embodiment, the body cavity is the abdominal, thoracic or uterine amniotic cavity. According to one exemplary embodiment, the body wall includes all the layers between the outside of the skin and the inside of the body cavity (i.e. skin to abdomen, skin to amniotic cavity). According to one exemplary embodiment, the biological membrane is a fascia or amnion of the uterine amniotic cavity.

According to one embodiment, in the deployed configuration, the arms are opened: the outwards deployment means deployed the arm (2) of each assembly outwardly relative to the longitudinal axis (A). In the deployed configuration, the deployed arms (2) press against the tissue surrounding the opening, thereby avoiding rupture of the surrounding tissue during the MIS procedure.

According to one embodiment, in the sealed configuration, the flaps are closed: the inwards deployment means deployed the flaps (1) of each assembly inwardly relative to the longitudinal axis (A). According to one embodiment, in the sealed configuration, the flaps are closed and the arms remains opened thereby ensuring watertight sealing of a body wall opening (13) subsequent to any type of MIS. The body wall opening (13) may cover a surface area as smaller as possible, ranging from 0.75 mm$^2$ to 710 mm$^2$ or from 0.75 to 320 mm$^2$. In one embodiment, said opening has a circular or oval shape.

According to one embodiment, said circular-shaped opening has a diameter ranging between 1 mm to 30 mm, or from 1 mm to 20 mm.

According to one embodiment, the at least two assemblies comprises a flap (1) connected to an arm (2), preferably directly connected. According to one embodiment, the flap (1) and the arm (2) of each assembly are integral or are mechanically connected together.

According to one embodiment, each flap (1) comprises an occluding portion (1.1) and a connecting portion (1.2). According to one embodiment, the occluding portion (1.1) and the connecting portion (1.2) are integral.

According to one embodiment, the occluding portions of the flaps (1.1) have a substantially semicircular or triangular shape (as illustrated in FIG. 1). According to one other embodiment, the occluding portions (1.1) have a shape configured or designed for allowing the free edges (1.11, 1.12) of the occluding portion (1.1) (i.e. those which are not connected to the connecting portion (1.2)) to be joined edge-to-edge when the flaps (1) are closed. (i.e. when the assemblies are in the sealed configuration).

According to one embodiment, the inner surface (1.21) of the connecting portion of the flaps (1.2) is curved inwardly (i.e. concave) in order to form or design a cylinder in the delivery configuration. According to one embodiment, the connecting portions of the flaps (1.2) are connected together, preferably via the lateral edges (1.22, 1.23).

According to one embodiment, the flaps (1) of each assembly have a length (from the proximal to the distal end of the flap (1)) ranging between 0.5 mm to 15 mm or from 0.5 to 10 mm in order to seal the surface of the opening.

According to one embodiment, each arm (2) comprises a connecting portion (2.1) and a pressing portion (2.2). According to one embodiment, the connecting portion (2.1) and the pressing portion (2.2) are integral.

According to one embodiment, the pressing portions (2.2) have substantially a circular, oval, triangular, rectangular, square shape or any designed shape to performed the deployed configuration, preferably a rectangular shape (as illustrated in FIGS. 1 and 3A).

According to one embodiment, the inner surface (2.21) of the pressing portion (2.2) is substantially flat in order to enhance the pressing surface when a membrane or a tissue lies against said inner surface (2.21) (as illustrated in FIGS. 3A and 3D).

According to one embodiment, the ratio between the length of the arm (2) of each assembly (from the proximal to the distal end of the arm) and the length of the flap (1) is ranging between 1 to 50, from 1 to 30, from 1 to 20, or from 5 to 15.

According to one embodiment, the connecting portion (1.2) of the flap (1) of each assembly is connected to the connecting portion (2.1) of the arm (2) of each assembly. According to one embodiment, said connection between the two connecting portions (1.2, 2.1) enables movement relative to each other. According to one embodiment, the connecting portions (1.2, 2.1) have any suitable shape known from one skilled in the art for enabling a relative movement between the flaps (1) and the arms (2) of each assembly. In an embodiment, the biomedical device comprises assembling means connected to the at least two assemblies, said assembling means being configured such that each connection between the two connecting portions of each assembly is located on a same plane transverse (or perpendicular) to the longitudinal axis (A).

According to one embodiment, the connecting portion (1.2) of the flap (1) of each assembly and the connecting portion (2.1) of the arm (2) of each assembly are integral. The movement between each portion is allowed due e.g. to the flexibility of the material or to the shape memory alloy behavior of the material.

According to one embodiment, the connecting portion (1.2) of the flap (1) of each assembly and the connecting portion (2.1) of the arm (2) of each assembly are connected by a mechanical means. In one embodiment, said mechanical means is a hinge. According to one embodiment, the connecting portions (1.2, 2.1) have complementary shapes. According to one embodiment, the connecting portion (1.2) of each flap (1) comprises a groove (1.24) and the connecting portion (2.1) of each arm (2) comprises a tongue (2.11) forming a tongue and groove connection. According to one embodiment, the connecting portions (1.2, 2.1) comprise a male and female pivot joint. According to one embodiment, the connecting portions (1.2, 2.1) are reversibly connected. According to one embodiment, the connecting portions (1.2, 2.1) are irreversibly connected in situ (e.g. due to an inclined groove 1.24, see FIG. 2).

According to one embodiment, the connecting portions (1.2, 2.1) (especially the tongue and groove connection or the pivot joint) are configured or designed for enabling a relative movement of the flap (1) relative to the arm (2) of each assembly from substantially 0 to substantially 90°. In particular the arms (2) rotate relative to the flaps (1) from substantially 180 to substantially 90° when the biomedical device switches from the delivery configuration to the deployed configuration and the flaps (1) relative to the arms (2) rotates from substantially 90 to substantially 180° when the biomedical device switches from the deployed configuration to the sealed configuration. According to one embodiment, the connecting portions (1.2, 2.1) are configured or designed for avoiding a relative movement exceeding substantially 90° between the flap (1) and the arm (2) of each assembly. According to an exemplary embodiment, the connecting portion (1.2) of the flap (1) of each assembly comprises an inclined plan (1.25) cooperating with an inclined plan (2.12) of the connecting portion (2.1) of the arm (2) of each assembly; thereby forming a V. According to one embodiment, said inclined plans (1.25, 2.12) exhibit an angle of substantially 45° in order to prevent a relative movement exceeding substantially 90°.

One object of the relative movement of the connecting portion (1.2, 2.1) is to enable the biomedical device of the invention to exhibit different configurations. Different configuration refers to the ability to switch from a delivery configuration (see FIG. 4) to a deployed configuration (see FIGS. 5A, 5B, and 8), and from a deployed configuration to a sealed configuration (see FIG. 7).

According to one embodiment, the biomedical device comprises at least 2, 3, 4, 5, 6, 7, 8, 9, 10, 11, 12 assemblies (i.e. at least 2, 3, 4, 5, 6, 7, 8, 9, 10, 11, 12 flaps (1) and at least 2, 3, 4, 5, 6, 7, 8, 9, 10, 11, 12 arms (2)).

According to one embodiment, the length of each flap (1), when measured in the delivery configuration in the direction of the longitudinal axis (B) is equal to the radius of the hollow cylinder formed by the at least two assemblies in the delivery configuration. In said embodiment, by manipulating the inwards deployment means (4), the flap of each assembly rotates relative to the arm and the free edges (1.11, 1.12) of the occluding portion (1.1) are joined edge-to-edge.

According to one embodiment, the length of each flap (1), when measured in the delivery configuration in the direction of the longitudinal axis (B) is less than the radius of the hollow cylinder formed by the at least two assemblies in the delivery configuration. In said embodiment, by manipulating the inwards deployment means (4), the flap of each assembly rotates relative to the arm so that the flap of each assembly are located in the same plane transverse to the longitudinal axis (A) and then the flap of each assembly translate within the said plane relative to each other so that the free edges (1.11, 1.12) of the occluding portion (1.1) are joined edge-to-edge. Said translation of the flaps enables to reduce the size of the opening performed for inserting the biomedical device. Indeed, the translation of the flaps, and thus the translation of the arms, moves the tissue surrounding the opening.

According to one embodiment, the flap (1) and the arm (2) of each assembly are made of a bioabsorbable and biocompatible material known by one skilled in the art. According to one embodiment, said bioabsorbable material is absorbed by natural mechanisms named biodegradation. According to one embodiment, the bioabsorbable material is totally absorbed in less than 1 month, 2 months, 3 months, 4 months, 6 months or 12 months. According to one embodiment, the flap (1) and the arm (2) of each assembly are made of a rigid bioabsorbable material. According to one embodiment, each free edge (1.11, 1.12) of each occluding portion (1.1) is coated with a soft material improving adhesion between the flaps (1) and waterproofness. According to one embodiment, said soft material is a hydrogel. According to one embodiment, said soft material is a biocompatible polymer. Said soft material is a cross-linked polymer with low affinity binding. According to one embodiment, said soft material is a poly-ester.

According to one embodiment, the bioabsorbable material is Polydioxanone (PDS) commercially available from Ethicon under the brand Absolok®. According to another embodiment, the bioabsorbable material is polyglycolic acid (PGA) or polylactic acid (PLA). In one embodiment, the bioabsorbable material is self-reinforcing (SR). In one embodiment, the bioabsorbable material is a copolymer of PLA, PGA and/or SR. In one embodiment, the bioabsorbable material is plain or chromic catgut. In one embodiment, the at least one bioabsorbable material is a composite material.

According to one embodiment, the flap (1) and the arm (2) of each assembly are made of a non-bioabsorbable and biocompatible material known by one skilled in the art, such as metal alloy (e.g. Nitinol, TA6V . . . ).

According to one embodiment, said bioabsorbable material is radio-transparent.

According to one embodiment, said non-bioabsorbable material is radio-transparent.

According to one embodiment, said bioabsorbable material is radio-opaque.

According to one embodiment, said non-bioabsorbable material is radio-opaque.

According to one embodiment, the biomedical device further comprises a membrane (5). According to one embodiment, the membrane (5) connects the arm (2) of each assembly. According to one embodiment, the membrane (5) is connected at least partly along the flat inner surface (2.21) of the pressing portion (2.2) of each arm (2). In one embodiment, the membrane (5) is connected along the full length of the inner surface (2.21) of the pressing portion (2.2) of the arms (2).

According to one embodiment, the membrane (5) is watertight. According to one embodiment, the membrane (5) is pressed against the distal surface of the biological tissue surrounding the body wall opening (13) due to the pressing portion (2.2) of the arm (2); thereby providing a watertight seal around the body wall opening (13) between the biomedical device and the body wall.

In one embodiment, the membrane (5) is connected to the arms (2) of each assembly by a mechanical means, for example the membrane (5) is sutured or glued.

In one embodiment, the membrane (5) has a circular, an oval, an hexagonal, an octagonal, a square shape, an annulus shape or any suitable shape for covering the distal surface area surrounding the body wall opening (13). In one embodiment, the membrane (5) is an annulus having an outer diameter substantially equal to the length of the assembly and an inner diameter substantially equal to the length of the flap (1) of each assembly.

According to one embodiment, the membrane (5) has a surface area which is ranging from 1335 to 1 838 538 mm$^2$, from 1 335 to 1 837 832 mm$^2$, from 1 to 679 291 mm$^2$, from 1 to 311 725 mm$^2$, from 1 mm$^2$ to o 85 530 mm$^2$. In one embodiment, the membrane (5) is made of a material resistant and flexible in order to be folded or crumpled without damage.

According to one embodiment, the membrane (5) is stretched out upon deployment of the arms (2) from the delivery configuration (see FIG. 4) to the deployed configuration (see FIGS. 5A and 5B).

In one embodiment, the membrane (5) is made of at least one bioabsorbable material. According to one embodiment, the bioabsorbable material is totally absorbed in less than 1 month, 2 months, 3 months, 4 months, 6 months or 12 months. In one embodiment, the membrane (5) is made of a copolymer of lactic and/or glycolic acids. According to one embodiment, the membrane (5) is made from polyglactine 910 commercially available from Ethicon under the brand Vicryl®. According to one embodiment, the membrane (5) is made from any suitable biologically compatible, bioabsorbable or non-bioabsorbable, flexible medical membrane, textile or mesh known by one skilled in the art for watertight sealing of tissue defects.

According to one embodiment, the assembling means is the membrane which can be plain or pierced like a net or a sieve. According to one embodiment, the assembling means is at least one second membrane or at least one elastic band or at least one thread or at least one ribbon, in the form of an annulus, connected, for instance sutured or glued, to each arm (2). According to one embodiment, the assembling means is connected to the arm (2) of each assembly. According to one embodiment, the assembling means is connected at least partly along the flat inner surface (2.21) of the pressing portion (2.2) of each arm (2). In one embodiment, the assembling means is connected along the full length of the inner surface (2.21) of the pressing portion (2.2) of the arms (2).

According to one embodiment, the assembling means comprise at least one membrane or at least one elastic band or at least one thread or at least one ribbon with any form connecting at least two assemblies.

According to one embodiment, the assembling means has an annulus shape. In one embodiment, the assembling means is an annulus having an inner diameter substantially equal or higher than the length along the longitudinal axis (B) of the flap (1) of each assembly.

According to one embodiment, each arm (2) can move from a closed position to an open position (thereby switching the biomedical device from the delivery to the deployed configuration). According to one embodiment, each flap (1) can move from an open position to a closed position (thereby switching the biomedical device from the deployed to the sealed configuration).

According to one embodiment, in the delivery configuration the flap (1) and the arm (2) of each assembly are aligned in the longitudinal axis (B), each assembly extends along a direction substantially parallel to the longitudinal axis (A) and the at least two assemblies together form or design a cylinder having the longitudinal axis (A). FIG. 4 illustrates an embodiment of the biomedical device in the delivery configuration. According to said embodiment, the 6 flaps (1) are opened and the 6 arms (2) are closed thereby forming a substantially cylindrical structure comprising a cylindrical inner hollow cavity. According to one embodiment, the biomedical device in said delivery configuration is enclosed in an outer hollow tube (10). According to one embodiment, the cylindrical inner hollow cavity formed by the biomedical device encloses an inner hollow tube (11), for example an inner trocar.

Advantageously, in the delivery configuration the assemblies are slidably mounted into an outer hollow tube (10) and can be mobilized along the inner hollow tube (11).

In one embodiment, in the delivery configuration, the biomedical device has a cylindrical shape having a diameter ranging from 1 mm to 30 mm, or from 1 to 20 mm.

According to one embodiment, in the deployed configuration, the flap (1) of each assembly remains in the delivery configuration and the arm (2) of each assembly is opened, i.e. is deployed outwardly and positioned at substantially 90° relative to their position in the delivery configuration as illustrated in FIGS. 5A and 5B.

According to one embodiment, the arms (2) in the deployed configuration are configured for deploying and stretching out the membrane (5) connected to said arms (2).

According to one embodiment, in the deployed configuration an inner hollow tube (11) is located in the cylindrical cavity formed by the opened flaps (1). In one embodiment, said inner hollow tube (11) maintains the flaps (1) in an open state by maintaining a pressure against the flaps (1) (see FIGS. 5A and 5B).

In one embodiment, the surface area covered by the opened arms (2) having a hollow disk shape in the deployed configuration is ranging from 1300 to 1 840 000 $mm^2$, from 1 to 680 000 $mm^2$, from 1 to 315 000 $mm^2$, from 1 to 90 000 $mm^2$. According to one embodiment, the total area covered by the biomedical device in the sealed configuration (i.e. covered by the closed flaps (1) and the deployed arm (2)) having a disk shaped is ranging from 2000 to 1 840 000 $mm^2$, from 700 to 680 000 $mm^2$, from 340 to 315 000 $mm^2$, from 90 to 90 000 $mm^2$.

According to one embodiment, the biomedical device is switched from the delivery configuration to the deployed configuration by means of an outwards deployment means (3). According to one embodiment, said outwards deployment means (3) enables to open the arms (2) after removal of the outer hollow tube (10).

According to one embodiment, said outwards deployment means (3) comprises any means known by one skilled in the art. According to one embodiment, said outwards deployment means (3) comprises a spring-loaded mechanism for controlling the opening of the arms (2).

According to one embodiment, at least one flap (1) of the biomedical device comprises a first passage (6.1) extending through the flap (1) from an opening in the outer surface of the flap (1) to an opening in the inner surface (1.21) of the flap (1). According to one embodiment, said first passage (6.1) is substantially vertical across the flap (1). According to one embodiment, said first passage (6.1) is substantially transverse through the flap (1), see FIG. 2D.

According to one embodiment, at least one arm (2) of the biomedical device comprises a first passage (6.2) extending through the arm from an opening in the proximal outer surface of the arm (2) to an opening in the distal outer surface of the arm (2). According to one embodiment, said first passage (6.2) is substantially longitudinal across the arm (2). According to one embodiment, said first passage (6.2) is substantially longitudinal through the arm (2).

According to one embodiment, the outwards deployment means (3) comprises at least one thread fixed at the opening in the proximal outer surface of at least one arm (2), passing through the first passage (6.2) of the arm (2) from the opening in the proximal outer surface of the arm (2) to the opening in the distal outer surface of the arm (2), passing through the first passage (6.1) of the flap (1) of the corresponding assembly from the opening in the outer surface of the flap (1) to the opening in the inner surface (1.21) of the flap (1) and extending out.

According to one embodiment, each flap (1) of the biomedical device comprises a first passage (6.1) extending through each flap (1) from an opening in the outer surface of the flap (1) to an opening in the inner surface (1.21) of the flap (1). According to one embodiment, each arm (2) of the biomedical device comprises a first passage (6.2) extending through each arm (2) from an opening in the proximal outer surface of the arm (2) to an opening in the distal outer surface of the flap (2). According to one embodiment, the outwards deployment means (3) comprises a thread for each assembly (1). According to one embodiment, half of the assemblies comprise said first passage (6.1) and second passage (6.2).

According to one embodiment, said thread is bioabsorbable. According to one embodiment, the at least one thread is configured for being pulled in order to open the arms (2) by rotation of the two connecting portions (1.2, 2.1). According to one embodiment, the outwards deployment means (3) is configured for being pulled in order to deploy the arms (2) and optionally the membrane (5).

According to one embodiment, the biomedical device further comprises a means for maintaining the outwards deployment means (3) deployed by keeping the at least one thread under tension. According to one embodiment, said means is a clip. According to one embodiment, said means is any surgical forceps. According to another embodiment, said means is V-shaped notch, preferably a V-shaped notch terminating in a hole sized to hold the thread.

According to one embodiment, in the sealed configuration, the flaps (1) of each assembly are closed (i.e. deployed inwardly relative to the longitudinal axis (A) and positioned at substantially 90° relative to relative to their position in the delivery configuration), and the arm (2) of each assembly remain in the deployed configuration.

In one embodiment, the surface area covered by the closed flaps (1) in the sealed configuration is ranging from to 0.75 $mm^2$ to 710 $mm^2$ or from 0.75 $mm^2$ to 320 $mm^2$. According to one embodiment, in the sealed configuration, the flap (1) and the arm (2) of each assembly are aligned along an axis transverse or perpendicular to the longitudinal axis (A) as illustrated in FIG. 7.

According to one embodiment, the biomedical device is switched from the deployed configuration to the sealed configuration by means of an inwards deployment means (4). According to one embodiment, said inwards deployment means (4) enables to close the flaps (1) after removal of an inner hollow tube (11). FIG. 6 illustrates an intermediate configuration of the biomedical device wherein the biomedical device is removed and the deployment means (4) progressively closes the flaps (1).

According to one embodiment, said inwards deployment means (4) comprises any means known by one skilled in the art. According to one embodiment, said inwards deployment means (4) comprises a spring-loaded mechanism for controlling the closing of the flaps (1).

According to one embodiment, the flap (1) of each assembly comprises a connecting passage (7) extending across a part of the flap (1), preferably across the distal part of the occluding portion (1.1) of the flap (1). According to one embodiment, said connecting passage (7) is substantially horizontal. According to one embodiment, said connecting passage (7) extends through the distal part of the occluding portion (1.1) of each flap (1).

According to one embodiment, at least one flap (1) of the assemblies comprises a second passage (8) extending through the flap (1) from the connecting passage (7) to an opening in the inner surface (1.21) of the flap (1). According to one embodiment, said second passage (8) is oblique. According to one embodiment, said second passage (8) is transverse. According to one embodiment, said opening in the inner surface (1.21) of the flap (1) is distal such that the lever arm between said opening and the connection between the arm and the flap enables the closing of the flap (1). According to one embodiment, each flap (1) comprises a first and second passage (6.1; 8).

According to one embodiment, the opening in the inner surface (1.21) of the flap (1) of the second passage (8) is distal such that during the closing of the flaps (1) by means of the inwards deployment means (4), the biomedical device does not translate, or to a small extent, relative to the surrounding tissue.

According to one embodiment, the inwards deployment means (4) comprises a thread (12) connecting the flap (1) of each assembly together through the connecting passage (7) of each flap (1), passing through the second passage (8) of one flap (1) from the connecting passage (7) to the opening in the inner surface (1.21) of said flap (1) and extending out.

According to one embodiment, the flap (1) comprising the second passage (8) comprises a second groove (1.26) on the inner surface (1.21) of the connecting portion (1.2) of said flap (1).

According to one embodiment, said thread is bioabsorbable. According to one embodiment, the thread is configured for being pulled in order to close the flaps (1) by rotation of the two connecting portions (1.2, 2.1). According to one embodiment, the inwards deployment means (4) is configured for being pulled in order to close the flaps (1).

According to one embodiment, the biomedical device further comprises a means for maintaining the inwards deployment means (4) deployed by keeping the thread (12) under tension. According to one embodiment, said means is a clip. According to one embodiment, said means is any surgical forceps. According to another embodiment, said means is V-shaped notch, preferably a V-shaped notch terminating in a hole sized to hold the thread. According to one embodiment, the said means for maintaining the inwards deployment means (4) deployed are located in the longitudinal axis (A) such that when closing the flaps by means of the inwards deployment means, the biomedical device does not translate, or to a small extent, relative to the surrounding tissue.

FIGS. 2A, 2B, 2C and 2D illustrate an exemplary embodiment of at least one flap (1) of the assembly, said flap (1) comprising:
  an occluding portion (1.1) comprising:
    a first free edge (1.11) and a second free edge (1.12) forming triangular shape;
    a first passage (6.1);
    a connecting passage (7);
    a second passage (8);
  and
  a connecting portion (1.2) comprising:
    an inner surface (1.21) configured for being pressed against the inner surface of a body cavity, and optionally to stretch a membrane (5);
    first and second lateral edges (1.22, 1.23);
    a first groove (1.24) configured for being connected to a compatible tongue e.g. of the arm (2.11) and enabling the relative movement of the flap (1);
    an inclined plan (1.25) configured or designed for blocking the relative movement between a flap (1) and an arm (2) when connected;
    a second grove (1.26) configured for passing a thread through the length of the flap (1).

FIGS. 3A, 3B, 3C, 3D and 3E illustrate an exemplary embodiment of at least one arm (2) of the assembly, said arm (2) comprising:
  a connecting portion (2.1) comprising:
    a tongue (2.11) compatible with the first groove (1.24) of the flap (1) described above;
    an inclined plan (2.12) configured or designed for cooperating with the inclined plan (1.25) of the flap (1) described above in order to prevent a relative movement exceeding substantially 90° between the flap (1) and the arm (2);
  and
  a pressing portion (2.2) comprising:
    an inner surface (2.21) configured for being pressed against the inner surface of the body cavity;
    a first passage (6.2).

As depicted in FIGS. 8, 9A and 9B, the biomedical device further comprises an anchoring ring (9), preferably having an outer diameter substantially equal to the length of one assembly in the delivery or sealed configurations along the longitudinal axis (B); said anchoring ring (9) comprising the means for maintaining the outwards and inwards deployment means (3, 4) deployed (e.g. maintaining the threads under tension).

According to one embodiment, the anchoring ring (9) has substantially a circular, oval, triangular, rectangular, annular, square shape or any suitable shape, preferably an annular shape (as illustrated in FIGS. 9A and 9B).

According to one embodiment, the anchoring ring (9) is positioned in the deployed and sealed configurations along or against the outside part of the opening perpendicular to the longitudinal axis (A) around the inner hollow tube.

According to one embodiment, the biomedical device further comprises a means for maintaining the outwards deployment means (3) deployed, preferably at least a clip or at least a surgical forceps or at least a V-shaped notch fixed to the anchoring ring (9) keeping at least one thread under tension. According to one embodiment, the biomedical device further comprises a means for maintaining the inwards deployment means (4) deployed, preferably at least a clip or at least a surgical forceps or at least a V-shaped notch fixed to the anchoring ring (9) keeping at least one thread under tension. According to one embodiment, the said means for maintaining the inwards deployment means (4) deployed are aligned in the longitudinal axis (A).

According to one embodiment, the anchoring ring (9) comprises two parts (9.1; 9.2) forming the final shape of the anchoring ring. Said two parts are connected by any connecting means (14) known by one skilled in the art, such as for example a tongue (14.1) and a blocking means (14.2).

According to one embodiment, as depicted in FIGS. 9A and 9B, the anchoring ring (9) comprises two parts (9.1; 9.2) each part comprises a tongue (14.1) and a blocking means (14.2) cooperating with the tongue (14.1) of the other part. Said blocking means (14.2) enable sliding and translation of the two parts relative to each other.

The present invention also relates a method for watertight sealing of an opening at the end of a minimally invasive surgery comprising the following steps:
  a) providing the biomedical device according to the present invention;
  b) slidably mounting said biomedical device, in the delivery configuration, between an outer hollow tube (10) enclosing the biomedical device and an inner hollow tube (11) enclosed by the biomedical device;

c) inserting the outer hollow tube (10) comprising the biomedical device and the inner hollow tube (11) through an opening formed into any body wall of a subject;

d) advancing the outer hollow tube (10) comprising the biomedical device and the inner hollow tube (11) inside a body cavity of a subject until the biomedical device is fully inserted into an interior space of the body;

e) advancing the biomedical device inside a body cavity of a subject;

f) removing the outer hollow tube (10); and g) opening the arms (2) using the outwards deployment means (3), thereby switching the biomedical device from the delivery configuration to the deployed configuration;

h) manipulating surgical instruments inserted through the inner hollow tube (11) and performing a surgical intervention;

i) removing the inner hollow tube (11); and j) closing the flaps (1) using the inwards deployment means (4), thereby switching the biomedical device from the deployed configuration to the sealed configuration.

According to one embodiment, the method also comprises after step g) the step of securing the arms (2) against the distal surface of the tissue surrounding the body wall opening (13) by holding the outwards deployment means (3) in a clip, surgical forceps or V-shaped notch; thereby locking in translation the device. According to one embodiment, the method also comprises after step g) the steps of pressing an anchoring ring (9) against the proximal surface of the biological tissue surrounding the body wall opening (13) and then securing the arms (2) against the distal surface of the tissue surrounding the body wall opening (13) by holding the outwards deployment means (3) in a clip, surgical forceps or V-shaped notch fixed on the anchoring ring (9); thereby locking in translation the device.

According to one embodiment, the method also comprises after step j) the step of securing the flaps (1) closed by holding the inwards deployment means (4) in a clip, surgical forceps or V-shaped notch; thereby locking in translation the device. According to one embodiment, the method also comprises after step j) the steps of pressing an anchoring ring (9) against the proximal surface of the biological tissue surrounding the body wall opening (13) and then securing the flaps (1) closed by holding the inwards deployment means (4) in a clip, surgical forceps or V-shaped notch fixed on the anchoring ring (9); thereby locking in translation the device. According to another embodiment, the method also comprises after step j) the steps of securing the flaps (1) closed by holding the inwards deployment means (4) in a clip, surgical forceps or V-shaped notch fixed on the anchoring ring (9) introduced after step g); thereby locking in translation the device.

According to one embodiment, the diameter of the inner hollow tube (11) is configured for enabling surgical instruments (e.g. an endoscope) to be inserted therethrough.

In one embodiment, in the deployed configuration (illustrated by FIGS. 5A and 5B), the biomedical device is configured for:
 (i) lying the membrane (5) stretched by the arms (2) against the tissue surrounding the opening to be sealed; and
 (ii) pressing the membrane (5) and the arms (2) against the tissue surrounding the opening to be sealed, thus enabling waterproofing.

In said deployed configuration, the arms (2) cover a surface area around the body wall opening (13). According to one embodiment, the surface area refers to the surface located between the proximal and distal ends of the arms (2). According to one embodiment, said surface area has the shape of a hollow disc.

The at least one thread of the outwards deployment means enables deployment as well as watertight pressure of the arms (2) connected to the membrane (5) against the inside (or distal) part of the body wall when said thread is hold under tension e.g. in the clip, surgical forceps or V-shaped notch.

According to one embodiment, in the deployed configuration, the inner hollow tube (11) maintains the flaps (1) in an open state and thus maintains the biomedical device in said deployed configuration. In one embodiment, the inner hollow tube (11) may be a trocar for performing MIS.

In the deployed configuration, a surgical intervention may be performed through the access port formed by the opened flaps (1). In said configuration, the opened arms (2) and the membrane (5), provide a tight sealing between said membrane (5) and the inner surface of the tissue surrounding the body wall opening (13).

Advantageously, said biomedical device provides a watertight and direct access port wherein surgical instruments may be introduced. It also minimizes the possible leakage of biological fluids circumferentially around the body wall opening. Finally, when tools located in the inner hollow tube (11) are manipulated, in order to perform a MIS for example. Moreover, the cylinder formed by the flaps (1) prevents the enlargement of said wall opening.

In one embodiment, in the sealed configuration (as illustrated in FIG. 7), the biomedical device is configured for:
 (i) lying the membrane (5) stretched by the arms (4) against the tissue surrounding the inside of the opening to sealed;
 (ii) pressing the membrane (5) and the arms (2) against the tissue surrounding inside of the opening to sealed, enabling waterproofing;
 (iii) sealing the opening by closing the flaps (1) thereby watertight sealing of the opening.

In one embodiment, the biomedical device switches to the sealed configuration when the inner tube (11) is removed from the biomedical device. For example, the inner hollow tube (11) is pulled while the arms (2) are maintained against the inner surface of the tissue surrounding the body wall opening (13).

In the sealed configuration, the flaps (1) are closed and joined together to form a watertight sealed structure.

According to one embodiment, the biomedical device in the sealed configuration is configured for being hold in place by means of the internal pressure of the body cavity which pushes and maintains the flaps (1) closed. According to one embodiment, at least one thread of the inwards deployment means (4) also prevents the flaps (1) to be re-opened in situ when said thread is hold e.g. in a clip, surgical forceps or V-shaped notch.

According to one embodiment, the anchoring ring (9) comprises the clip or surgical forceps or V-shaped notch maintaining the threads (12) of the inwards (4) and outwards (3) deployment means is configured for being located against the outer surface of the tissue surrounding the body wall opening (13). This anchoring ring (9) presses the body wall on the other side of the arms (2) and enables waterproofing and watertight sealing of the body wall opening (13).

In another aspect, the invention also relates to a kit of parts comprising:
- an outer hollow tube (10);
- an inner hollow tube (11); wherein said inner hollow tube (11) has a smaller diameter than the outer hollow tube (10);
- a biomedical device according to the present invention; and
- optionally, an anchoring ring (9) comprising means for maintaining the outwards and inwards deployment means (3, 4) deployed;

wherein said biomedical device is configured:
- for being positioned between said inner and outer hollow tubes (10, 11) in a delivery configuration; the inner hollow tube (11), the outer hollow tube (10) and the biomedical device having the same longitudinal axis (A) in said delivery configuration; and
- for being axially moveable along said longitudinal axis (A), especially relative to the outer hollow tube and the inner hollow tube.

In one embodiment, the outer hollow tube (10) and/or the inner hollow tube (11) is made from a flexible biocompatible material. In one embodiment, the outer hollow tube (10) and/or the inner hollow tube (11) is made from a biocompatible rigid material. In one embodiment, the inner hollow tube (11) is a trocar. In one embodiment, the inner hollow tube (11) is a cannula.

BRIEF DESCRIPTION OF THE DRAWINGS

The foregoing summary and detailed description of the invention will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

REFERENCES

Figure 1:
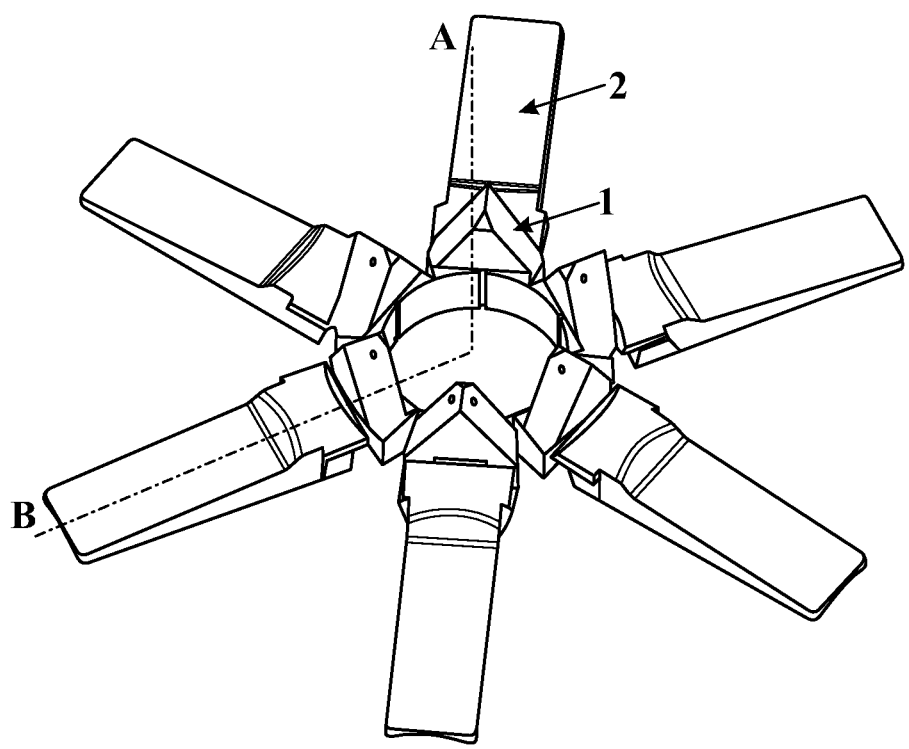
FIG. 1 is showing a perspective view of the biomedical device in the deployed configuration.
Figure 2A:
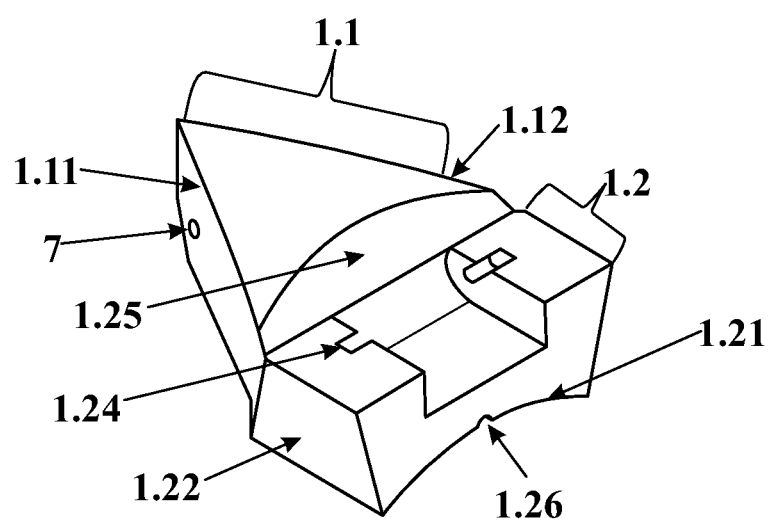
FIG. 2A shows a perspective view of a flap.
Figure 2B:
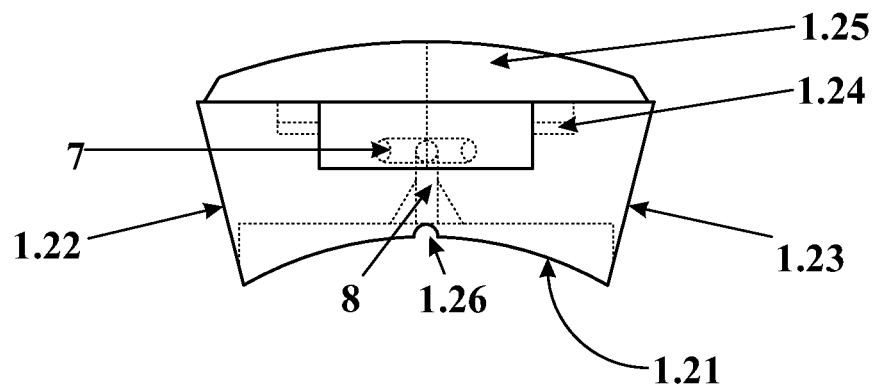
FIG. 2B shows a projection view of a flap along the width.
Figure 2C:
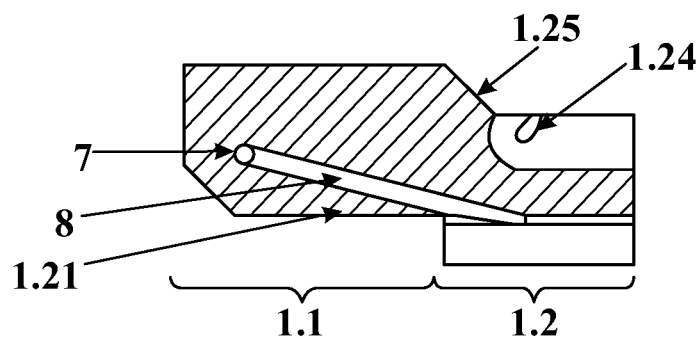
FIG. 2C shows a longitudinal cross section of a flap.
Figure 2D:
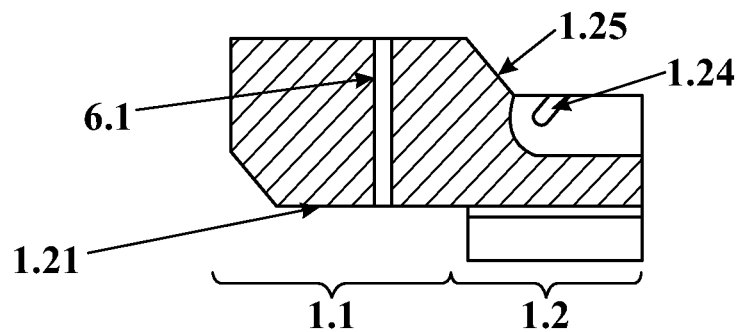
FIG. 2D shows a longitudinal cross section of a flap.
Figure 3A:
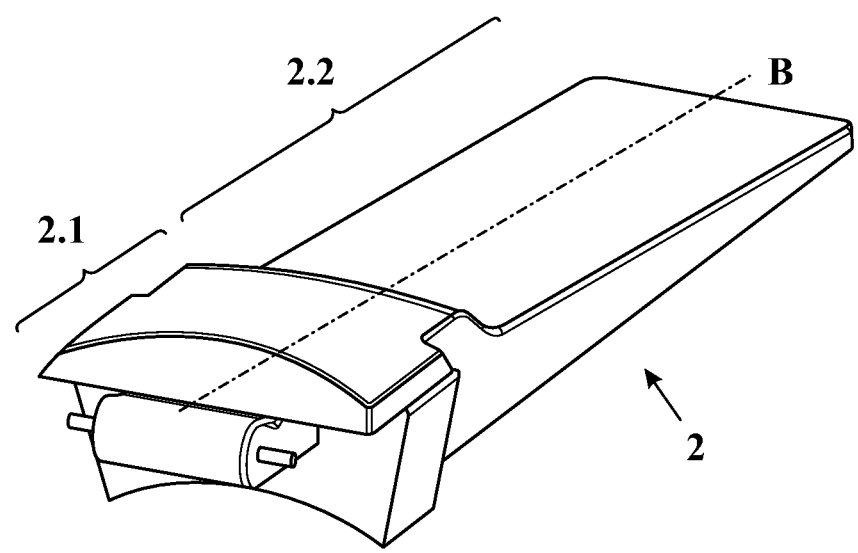
FIG. 3A shows a perspective view of an arm.
Figure 3B:
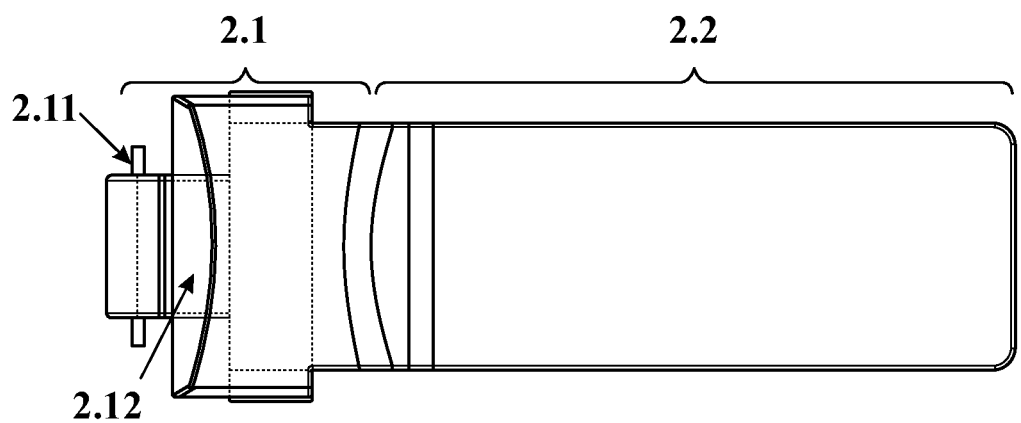
FIG. 3B shows a top view of an arm.
Figure 3C:
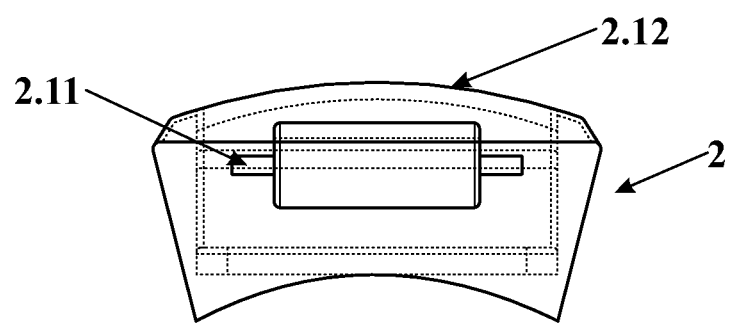
FIG. 3C shows a projection view of an arm along the width.
Figure 3D:
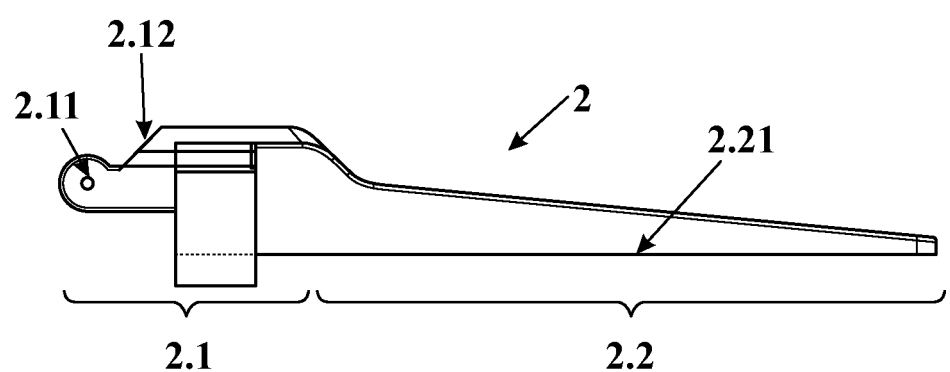
FIG. 3D shows a side view of an arm along the length.
Figure 3E:
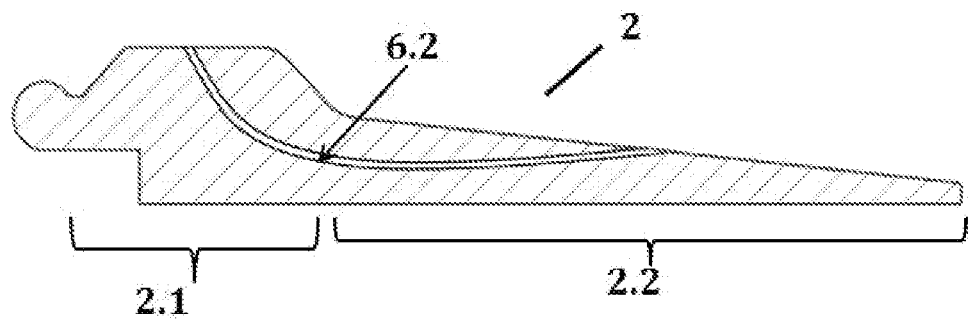
FIG. 3E shows a longitudinal cross section of an arm.
Figure 4:
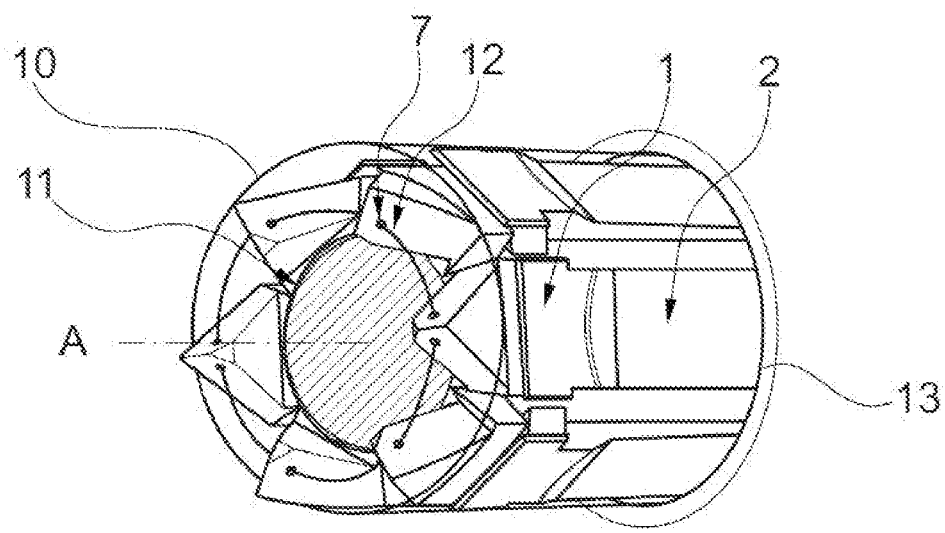
FIG. 4 shows a perspective view of the biomedical device in the delivery configuration.
Figure 5A:
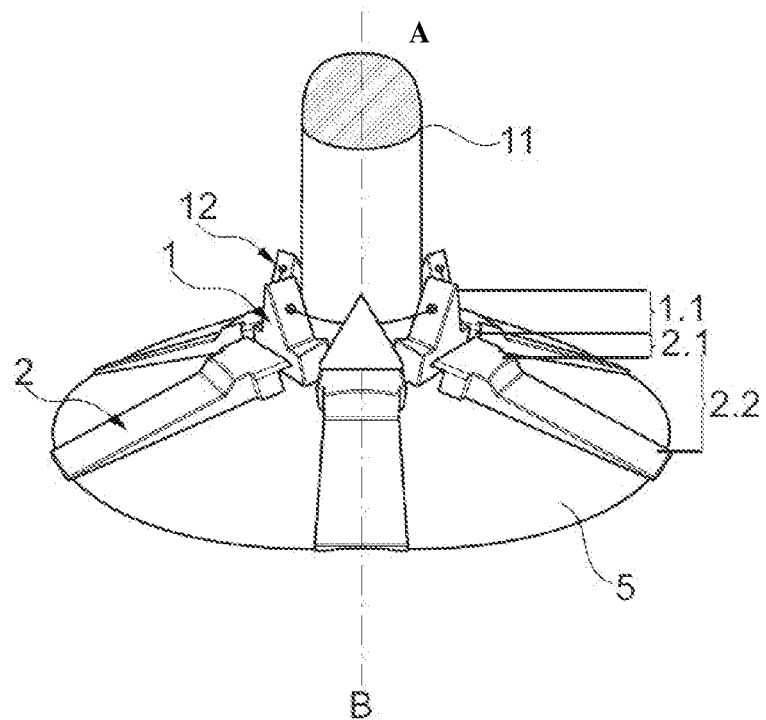
FIG. 5A shows a perspective view of the biomedical device in the deployed configuration.
Figure 5B:
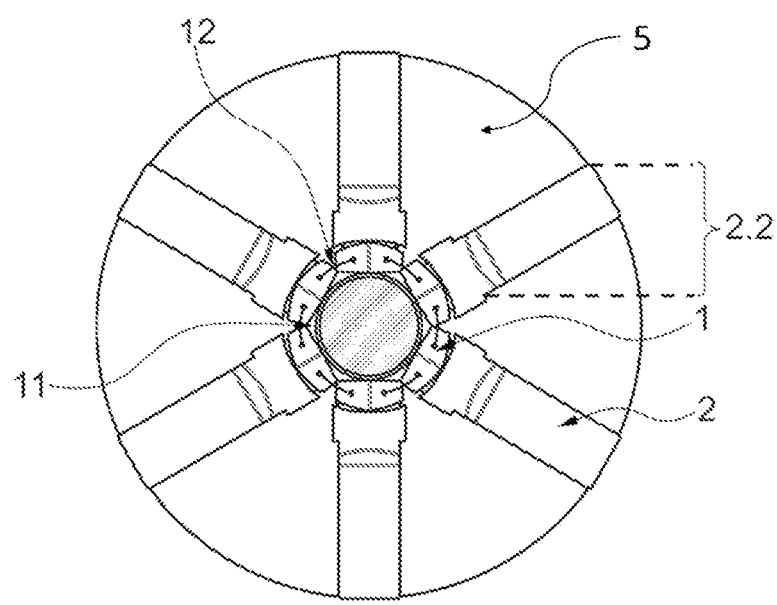
FIG. 5B shows the biomedical device in the deployed configuration, view from the body cavity.
Figure 6:
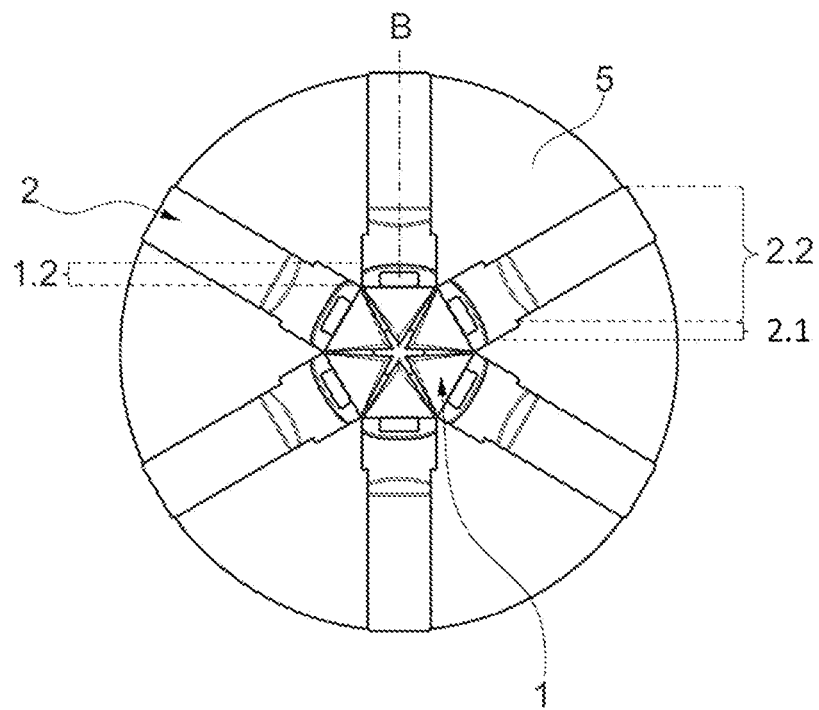
FIG. 6 shows the biomedical device in an intermediary step between the deployed configuration and the sealed configuration, view from the body cavity.
Figure 7:
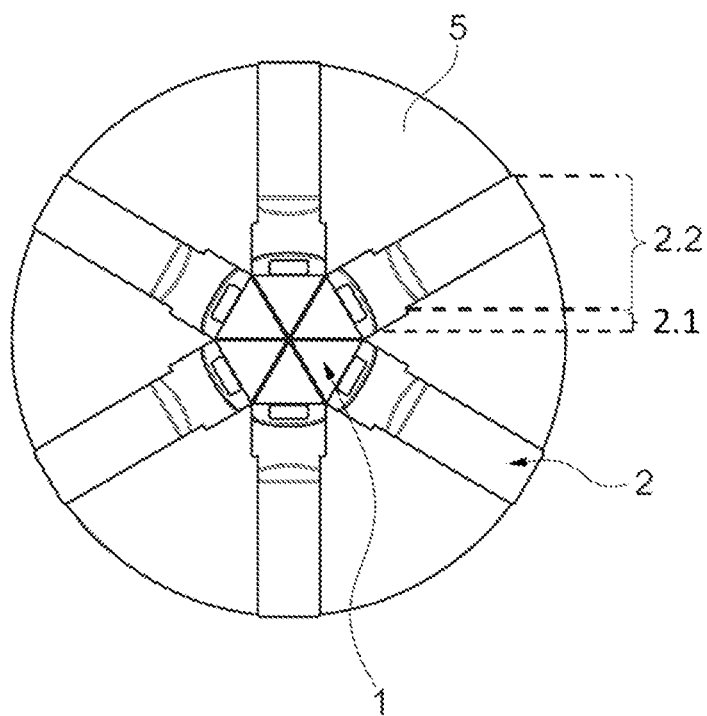
FIG. 7 shows the biomedical device in the sealed configuration, view from the body cavity.
Figure 8:
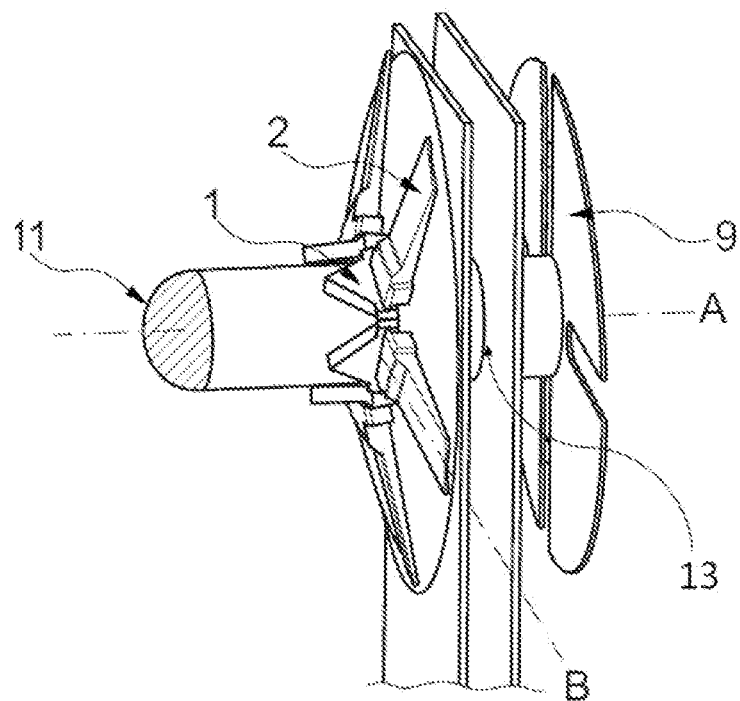
FIG. 8 shows a view of the biomedical device comprising a cylindrical anchoring ring.
Figure 9A:
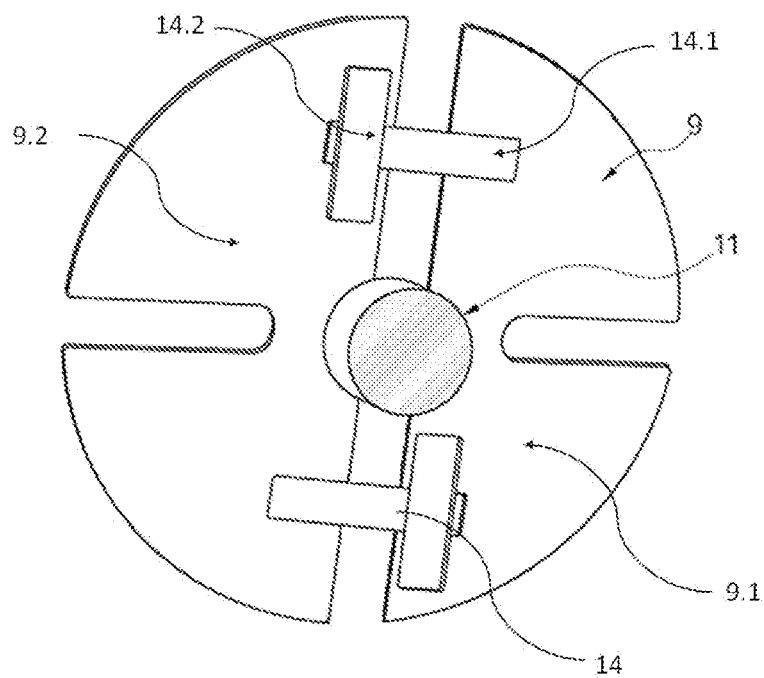
FIGS. 9A and 9B shows a view of an anchoring ring in the deployed (9A) and sealed configuration (9B).
Figure 9B:
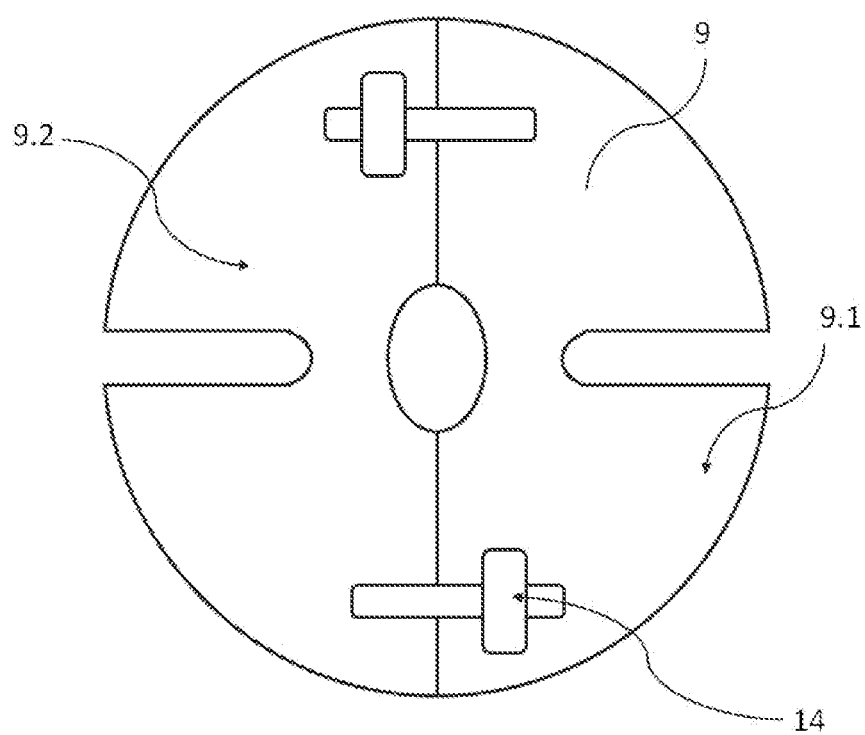

A Longitudinal axis of the hollow tube
B Longitudinal axis of the arms
1 Flap
1.1 Occluding portion of the flap
1.11 First free edge of the occluding portion
1.12 Second free edge of the occluding portion
1.2 Connecting portion of the flap
1.21 Inner surface of the connecting portion
1.22 First lateral edge of the connecting portion
1.23 Second lateral edge of the connecting portion
1.24 First groove of the connecting portion
1.25 Inclined plan of the connecting portion
1.26 Second grove of the connecting portion
2 Arm
2.1 Connecting portion of the arm
2.11 Tongue of the connecting portion
2.12 Inclined plan of the connecting portion
2.2 Pressing portion
2.21 Inner surface of the pressing portion
3 Outwards deployment means
4 Inwards deployment means
5 Watertight membrane
6.1 First passage of the flap
6.2 First passage of the arm
7 Connecting passage of the flap
8 Second passage of the flap
9 Anchoring ring
9.1 First part of the anchoring ring
9.2 Second part of the anchoring ring
10 Outer hollow tube
11 Inner hollow tube
12 Thread of the inwards deployment means
13 Body wall opening
14 Connecting means of the anchoring ring
14.1 Tongue
14.2 Blocking means

The invention claimed is:

1. A biomedical device for watertight sealing of an opening in a subject during a minimally invasive surgery procedure, the biomedical device configured for being introduced in said subject by an outer hollow tube and comprising:
- at least two assemblies, each assembly comprising one flap as a proximal part, and one arm as a distal part; and
- assembling means connected to the at least two assemblies, said assembling means being configured such that the proximal part of each assembly is located in a plane perpendicular to a reference axis A, wherein,
- said one arm of each assembly includes a first connection portion and said one flap of each assembly has a second connection portion, the first connection portion and the second connection portion forming a hinge,
- the hinge connecting the first connection portion of said one arm to the second connection portion of said one flap such that an axis of connection is formed at the hinge with said one arm being rotatably connected to said one flap between a first relative position in which the arm and the flap form an angle of substantially 180° and a second relative position in which the arm and the flap form an angle of substantially 90°,
- the assemblies each
  - having a delivery configuration, a deployed configuration, and a sealed configuration;
  - the assemblies each having i) outwards deployment means for switching from the delivery configuration to the deployed configuration, and ii) inwards deployment means for switching from the deployed configuration to the sealed configuration; wherein:

in the delivery configuration, the flap and the arm of each assembly are oriented parallel to the reference axis A, each assembly extends along the direction substantially parallel to the reference axis A, and the at least two assemblies together form a hollow cylinder for receiving an inner hollow tube therethrough; an axis of the inner hollow tube coinciding with the reference axis A, the flap and the arm forming an angle of substantially 180°;

in the deployed configuration, the flap of each assembly remains parallel to the reference axis A along the inner hollow tube, and the arm of each assembly is deployed outwardly relative to the reference axis A and positioned at substantially 90° relative to the reference axis A, the flap and the arm forming an angle of substantially 90°; and in the sealed configuration, the flap of each assembly is deployed inwardly relative to the reference axis A and positioned at substantially 90° relative to the reference axis A, such that the flaps are joined in an edge to edge arrangement thereby closing and sealing said opening in a watertight manner, and the arm of each assembly remains positioned at substantially 900 relative to the reference axis A, the flap and the arm forming an angle of substantially 180°.

2. The biomedical device according to claim 1, wherein the assembling means is a membrane, connecting the arm of each assembly, which membrane is stretched out upon deployment of the arms from the delivery configuration to the deployed configuration.

3. The biomedical device according to claim 2, wherein the membrane, the outwards and/or the inwards deployment means are made from a bioabsorbable material.

4. The biomedical device according to claim 3, wherein the bioabsorbable material is polyglactine 910.

5. The biomedical device according to claim 2, wherein the membrane is plain or wherein the membrane is pierced.

6. The biomedical device according to claim 1, comprising 2, 3, 4, 5, 6, 7, 8, 9, 10, 11 or 12 assemblies.

7. The biomedical device according to claim 1, wherein each assembly is made from a bioabsorbable material.

8. The biomedical device according to claim 7, wherein the bioabsorbable material is polydioxanone (PDS).

9. The biomedical device according to claim 1, further comprising a means for maintaining the outwards deployment means deployed, and further comprising a means for maintaining the inwards deployment means deployed, and further comprising an anchoring ring having an outer diameter substantially equal to a length of one assembly in the delivery configuration in the direction of the arms; said anchoring ring comprising the means for maintaining the outwards and inwards deployment means deployed.

10. The biomedical device according to claim 1, wherein the assembling means is selected among at least one membrane, at least one elastic band, at least one thread or at least one ribbon.

11. The biomedical device according to claim 1, wherein the flaps have a triangular shape.

12. The biomedical device according to claim 1, wherein the inward deployment means is configured for being pulled in order to close the flaps.

13. The biomedical device according to claim 1, wherein the first connection portion and the second connection portion have complementary portions that together define the hinge as a tongue and groove connection.

14. The biomedical device according to claim 1, wherein the first connection portion and the second connection portion have complementary portions that together define the hinge as a male and female pivot joint.

15. A biomedical device for watertight sealing of an opening in a subject during a minimally invasive surgery procedure, the biomedical device configured for being introduced in said subject by an outer hollow tube and comprising:
at least two assemblies, each assembly comprising one flap as a proximal part, and one arm as a distal part, said one arm being connected to said one flap; and
assembling means connected to the at least two assemblies, said assembling means being configured such that the proximal part of each assembly is located in a plane perpendicular to a reference axis A;
the assemblies each
having a delivery configuration, a deployed configuration, and a sealed configuration;
the assemblies each having i) outwards deployment means for switching from the delivery configuration to the deployed configuration, and ii) inwards deployment means for switching from the deployed configuration to the sealed configuration; wherein:
in the delivery configuration, the flap and the arm of each assembly are oriented parallel to the reference axis A, each assembly extends along a direction substantially parallel to the reference axis A, and the at least two assemblies together form a hollow cylinder for receiving an inner hollow tube therethrough; an axis of the inner hollow tube coinciding with the reference axis A;
in the deployed configuration, the flap of each assembly remains parallel to the reference axis A along the inner hollow tube, and the arm of each assembly is deployed outwardly relative to the reference axis A and positioned at substantially 90° relative to the reference axis A; and
in the sealed configuration, the flap of each assembly is deployed inwardly relative to the reference axis A and positioned at substantially 90° relative to the reference axis A, such that the flaps are joined in an edge to edge arrangement thereby closing and sealing said opening in a watertight manner, and the arm of each assembly remains positioned at substantially 90° relative to the reference axis A,
wherein at least one flap comprises a first passage extending through the flap from an opening in an outer surface of the flap to an opening in an inner surface of the flap; and wherein at least one arm comprises a first passage extending through the arm from an opening in a proximal outer surface of the arm to an opening in a distal outer surface of the arm.

16. The biomedical device according to claim 15, wherein the outwards deployment means comprises at least one thread fixed at the opening in the proximal outer surface of the arm, passing through the first passage of the arm from the opening in the proximal outer surface of the arm to the opening in the distal outer surface of the arm, passing through the first passage of the flap of a corresponding assembly from the opening in the outer surface of the flap to the opening in the inner surface of the flap and extending out.

17. The biomedical device according to claim 15, wherein the flap of each assembly comprises a connecting passage extending across a part of the flap.

18. The biomedical device according to claim 17, wherein at least one flap comprises a second passage extending through the flap from the connecting passage to an opening in the inner surface of the flap.

19. The biomedical device according to claim 18, wherein the inwards deployment means comprises a thread connecting the flap of each assembly together through its connecting passage, passing through the second passage of one flap from the connecting passage to the opening in the inner surface of said flap and extending out.

20. A biomedical device for watertight sealing of an opening in a subject during a minimally invasive surgery procedure, the biomedical device configured for being introduced in said subject by an outer hollow tube and comprising:
  at least two assemblies, each assembly comprising one flap as a proximal part, and one arm as a distal part, said one arm being connected to said one flap; and
  assembling means connected to the at least two assemblies, said assembling means being configured such that the proximal part of each assembly is located in a plane perpendicular to a reference axis A;
  the assemblies each
    having a delivery configuration, a deployed configuration, and a sealed configuration;
  the assemblies each having i) outwards deployment means for switching from the delivery configuration to the deployed configuration, and ii) inwards deployment means for switching from the deployed configuration to the sealed configuration; wherein:
  in the delivery configuration, the flap and the arm of each assembly are oriented parallel to the reference axis A, each assembly extends along a direction substantially parallel to the reference axis A, and the at least two assemblies together form a hollow cylinder for receiving an inner hollow tube therethrough; an axis of the inner hollow tube coinciding with the reference axis A;
  in the deployed configuration, the flap of each assembly remains parallel to the reference axis A along the inner hollow tube, and the arm of each assembly is deployed outwardly relative to the reference axis A and positioned at substantially 90° relative to the reference axis A; and
  in the sealed configuration, the flap of each assembly is deployed inwardly relative to the reference axis A and positioned at substantially 90° relative to the reference axis A, such that the flaps are joined in an edge to edge arrangement thereby closing and sealing said opening in a watertight manner, and the arm of each assembly remains positioned at substantially 90° relative to the reference axis A,
  wherein the flap of each assembly comprises a connecting passage extending across a distal part of the flap.

21. A biomedical device for watertight sealing of an opening in a subject during a minimally invasive surgery procedure, the biomedical device configured for being introduced in said subject by an outer hollow tube and comprising:
  at least two assemblies, each assembly comprising one flap as a proximal part, and one arm as a distal part, said one arm being connected to said one flap; and
  assembling means connected to the at least two assemblies, said assembling means being configured such that the proximal part of each assembly is located in a plane perpendicular to a reference axis A;
  the assemblies each
    having a delivery configuration, a deployed configuration, and a sealed configuration;
  the assemblies each having i) outwards deployment means for switching from the delivery configuration to the deployed configuration, and ii) inwards deployment means for switching from the deployed configuration to the sealed configuration; wherein:
  in the delivery configuration, the flap and the arm of each assembly are oriented parallel to the reference axis A, each assembly extends along a direction substantially parallel to the reference axis A, and the at least two assemblies together form a hollow cylinder for receiving an inner hollow tube therethrough; an axis of the inner hollow tube coinciding with the reference axis A;
  in the deployed configuration, the flap of each assembly remains parallel to the reference axis A along the inner hollow tube, and the arm of each assembly is deployed outwardly relative to the reference axis A and positioned at substantially 90° relative to the reference axis A; and
  in the sealed configuration, the flap of each assembly is deployed inwardly relative to the reference axis A and positioned at substantially 90° relative to the reference axis A, such that the flaps are joined in an edge to edge arrangement thereby closing and sealing said opening in a watertight manner, and the arm of each assembly remains positioned at substantially 90° relative to the reference axis A,
  further comprising at least one of the group consisting of i) a means for maintaining the outwards deployment means deployed, and ii) a means for maintaining the inwards deployment means deployed.

22. The biomedical device according to claim 21, wherein the biomedical device comprising the means for maintaining the outwards deployment means deployed, the means for maintaining the outwards deployment means deployed is at least a clip or at least a surgical forceps or at least a V-shaped notch configured for keeping at least one thread under tension.

23. The biomedical device according to claim 21, wherein the biomedical devices comprises the means for maintaining the inwards deployment means deployed.

24. The biomedical device according to claim 23, wherein the means for maintaining the inwards deployment means deployed are at least a clip or at least a surgical forceps or at least a V-shaped notch configured for keeping at least one thread under tension.

25. A kit of parts comprising:
  a biomedical device according to claim 1;
  said outer hollow tube;
  said inner hollow tube, wherein said inner hollow tube has a smaller diameter than the outer hollow tube;
  wherein said biomedical device is configured for being positioned between said inner and outer hollow tubes in said delivery configuration wherein the inner hollow tube and the outer hollow tube are oriented parallel to the reference axis A and are axially moveable along said reference axis A.

26. The kit of parts according to claim 25, wherein the kit of parts further comprises an anchoring ring.

\* \* \* \* \*